March 5, 1935. P. C. MOHN Plant Pat. 124

ORANGE TREE

Filed Dec. 11, 1934

Inventor.
P. C. Mohn
By Robb & Robb
Attorneys

Patented Mar. 5, 1935

Plant Pat. 124

UNITED STATES PATENT OFFICE

124

ORANGE TREE

Pearl C. Mohn, Anaheim, Calif.

Application December 11, 1934, Serial No. 757,030

1 Claim. (Cl. 47—62)

The present discovery relates to orange trees and especially to a new and distinct variety of orange tree originated as a bud sport or mutation occurring in a tree in my orchard of the well known variety of Valencia oranges, and propagated by budding or grafting.

This new variety of orange discovered and propagated by me resembles the Valencia variety in fruit and tree characteristics except that the fruit is seedless and my new variety is somewhat more vigorous, and improved as to eating quality. It is here noted that the normal Valencia orange has approximately four to eight seeds each as distinguished from the unvarying seedlessness of my new variety.

Observation of the new characteristics above referred to over a number of consecutive seasons definitely indicates that said characteristics are permanent.

The accompanying illustration represents some of the fruit of my new variety, the foliage and wood of the tree being omitted as they do not form novel features of the new variety and correspond to those of the known Valencia.

Figure 1:
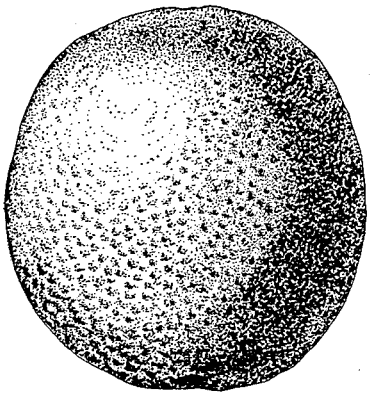
Figure 2:
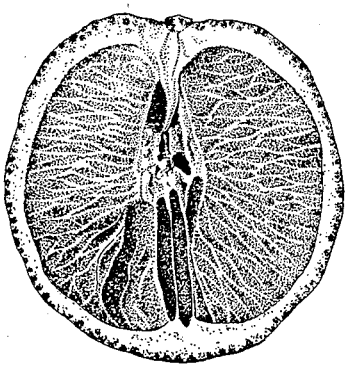
Figure 3:
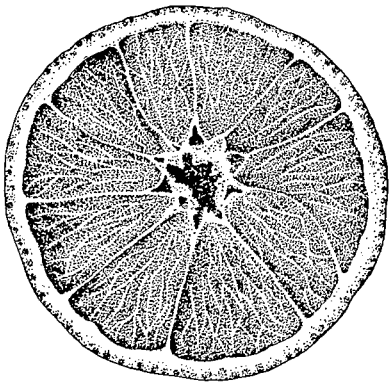

Fig. 1 is a side elevation and Figs. 2 and 3 longitudinal and transverse sections, respectively.

The following is a detailed description of this new variety or orange tree:

*Tree*

Large—vigorous—spreading—open top—productive—regular bearer.

*Trunk* stocky.

*Branches* stocky—much divided—lacking on old wood—new wood vegetative growth (suckers) slight.

*Leaves* medium thickness—large—dense—dark green—unifoliate—crenate — elliptical — bluntly pointed; petioles narrowly winged.

*Flowers* normally bloom in March or April—solitary.

*Fruit*

*Size* uniform; circumference from 6 to 12 inches; diameter from to 2 to 3½ inches.

*Form* uniform—symmetrical — regular — globose.

Base: rounded; smooth.

Apex: slightly depressed or even truncate.

Navel: wanting.

*Stem* medium size; medium slenderness; light green color; position straight.

*Calyx* even; segments 5 in number; acute.

*Rind* adherent to pulp; close early and late in season; surface smooth.

*Thickness* about $\frac{3}{16}$ inch.

*Flavor* very good.

*Color* orange; *Bloom* abundant.

*Oil cells* small—even.

*Segments* number 11 to 13; *Size* uniform; *Dorsal surface* rounded; *Segment walls* thin—tender.

*Flesh color:*

Texture fine—tender.

*Rag in flesh* medium; *Vesicles* long—broad; *Form* spindle.

*Juice* abundant—evenly distributed in section.

*Color* orange.

*Flavor* subacid—rich.

*Quality* best.

*Seeds,* wanting.

*Pith* almost solid; *Thickness* ⅜ inch.

*Season* same as Valencia variety under comparable conditions.

*Keeping quality* good.

*Shipping quality* good.

*Resistance to diseases* good.

I claim:

A new and distinct variety of orange tree as described, characterized by the seedlessness of its fruit, as shown.

PEARL C. MOHN.